US00PP33922P2

(12) United States Plant Patent
Ranney et al.

(10) Patent No.: US PP33,922 P2
(45) Date of Patent: Feb. 1, 2022

(54) ***AZALEA* PLANT 'NCRX8'**

(50) Latin Name: ***Rhododendron* hybrid**
Varietal Denomination: NCRX8

(71) Applicant: North Carolina State University, Raleigh, NC (US)

(72) Inventors: Thomas Green Ranney, Arden, NC (US); Darren Touchell, Raleigh, NC (US); Irene Palmer, Raleigh, NC (US); Andra Nus, Raleigh, NC (US); Nathan P. Lynch, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/343,204

(22) Filed: Jun. 9, 2021

(51) Int. Cl.
*A01H 6/38* (2018.01)
*A01H 5/00* (2018.01)

(52) U.S. Cl.
USPC ..... Plt./240

(58) Field of Classification Search
USPC ..... Plt./240
See application file for complete search history.

*Primary Examiner* — Annette H Para
(74) *Attorney, Agent, or Firm* — Cassandra Bright

(57) ABSTRACT

A new and distinct cultivar of *Rhododendron* plant named 'NCRX8' having prolific, bright cherry-red single flowers, cold hardy to USDA Zone 6b, consistent Fall reblooming, and a dense, compact habit. The new cultivar is a *Rhododendron*, suitable for ornamental garden purposes.

2 Drawing Sheets

Latin name of the genus and species: The Latin name of the novel plant variety disclosed herein is *Rhododendron* hybrid.

Variety denomination: 'NCRX8'.

The inventive hybrid was selected from seedlings derived from a controlled cross between evergreen azaleas H2009-242-026 (female, unpatented experimental hybrid) and H2009-308-006 (male, unpatented experimental hybrid). Prior to the designation of the varietal denomination, 'NCRX8' was referred to by its experimental code: H2014-136-152.

BACKGROUND OF THE INVENTION

The present invention comprises a new and distinct hybrid evergreen azalea cultivar hereinafter referred to by the cultivar name 'NCRX8'. This hybrid azalea was developed by a controlled breeding program at North Carolina State University, in Mills River, N.C. 'NCRX8' was selected for its single, cherry-red flowers, floriferousness, dense and compact growth habit, and consistent Fall reblooming. It was selected from the controlled, hand pollination of emasculated female experimental hybrid H2009-242-026 (unpatented) and male/pollen parent experimental hybrid H2009-308-006 (unpatented). 'NCRX8' was selected from this population of seedlings after 5 years in trials at the Mountain Horticultural Crops Research and Extension Center in Mills River, N.C.

Container trials were conducted using pine bark media supplemented with 1.04 $kg \cdot m^{-3}$ dolomitic lime, 0.74 $kg \cdot m^{-3}$ granulated micronutrients (Micromax; ICL Specialty Fertilizers, Tel Aviv, Israel) and top-dressed with 5- to 6-month slow-release fertilizer (Osmocote Plus 15-9-12, ICL Specialty Fertilizers). Full-sun field trials were conducted in plastic-covered, bark-amended clay soils with minimum winter temperatures of −2° F. (−19° C.) and maximum summer temperatures 98° F. (37° C.). The first asexual propagation of 'NCRX8' occurred in 2015 by rooting stem cuttings at the North Carolina State University Mountain Horticultural Crops Research Station, Mills River, N.C. 'NCRX8' roots readily from firm softwood cuttings treated with a basal dip of 3,000-5,000 ppm indole butyric acid (potassium salt) in water. 'NCRX8' has been found to retain its distinctive characteristics through successive asexual propagations over 6 years.

SUMMARY OF THE INVENTION

The following are the unique combination of characteristics of this new cultivar when grown under standard horticultural practices at North Carolina State University, Mountain Horticultural Crops Research Station, Mills River, N.C.

1. Bright, cherry-red single flowers.
2. Cold hardy to USDA Zone 6b.
3. Dense, compact habit.
4. Consistent Fall reblooming.

COMPARISON WITH PARENTS

Records of the parent variety characteristics are not available. The inventor cannot make a comparison to either the seed or pollen parent.

COMPARISON WITH COMMERCIAL CONTROLS

TABLE 1

| Plant | Flower Color and Type | Habit | Additional characters |
|---|---|---|---|
| *Rhododendron* 'Conlen' U.S. Plant Pat. No. 11,628 P | Red, single/semi-double flowers with some petaloids. RHS Red Group 46B. | Mid-sized/large 120-150 × 120-150 cm | Hardy to Zone 7 |

TABLE 1-continued

| Plant | Flower Color and Type | Habit | Additional characters |
|---|---|---|---|
| *Rhododendron* 'Conleb' U.S. Plant Pat. No. 10,581 | Red single semi-double flowers with some petaloids RHS Red Group 44A. | Mid-sized/large 120 × 140 cm | Hardy to Zone 7 |
| *Rhododendron* 'Conleo' U.S. Plant Pat. No. 11,640 | Red/salmon semi-double flower with some petaloids RHS Red Group 44D | Mid-sized, large 150-180 × 150-180 cm | Hardy to Zone 7 |
| *Rhododendron* 'NCRX8' | Cherry red single flowers, profuse flower display RHS Red Group 53B. | Compact, prostrate 75 × 90-120 cm | Hardy to Zone 6b |

BRIEF DESCRIPTION OF THE DRAWINGS

'NCRX8' is illustrated by the accompanying photographs, which show the plant's form, foliage, and inflorescences. The colors shown are as true as can be reasonably obtained by conventional photographic procedures. Colors in the photographs may differ slightly from the color values cited in the detailed botanical description, which accurately describe the new hybrid *Rhododendron.*

DETAILED BOTANICAL DESCRIPTION

Figure 1:
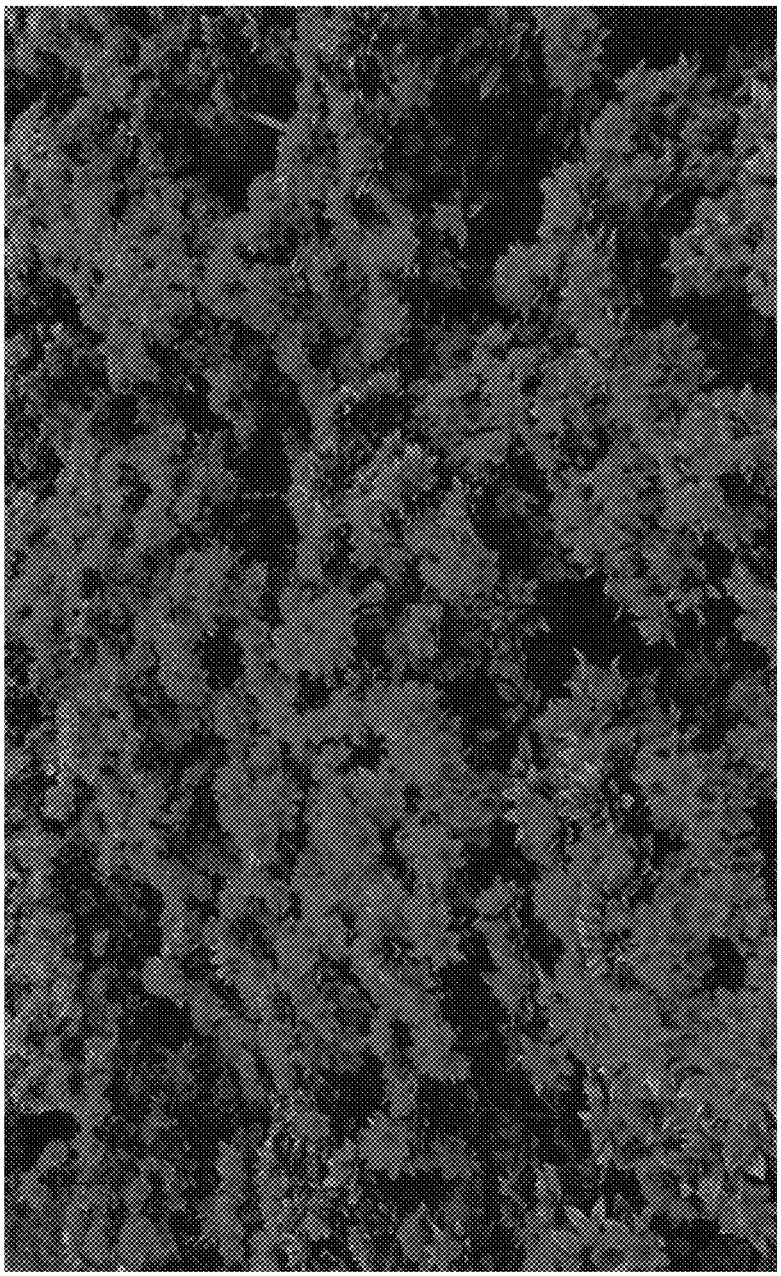
FIG. 1 Image showing flowering plants in 3-gallon containers; image taken from 3-year-old container plants grown in Grand Haven, Mich., in 2020.
Figure 2:
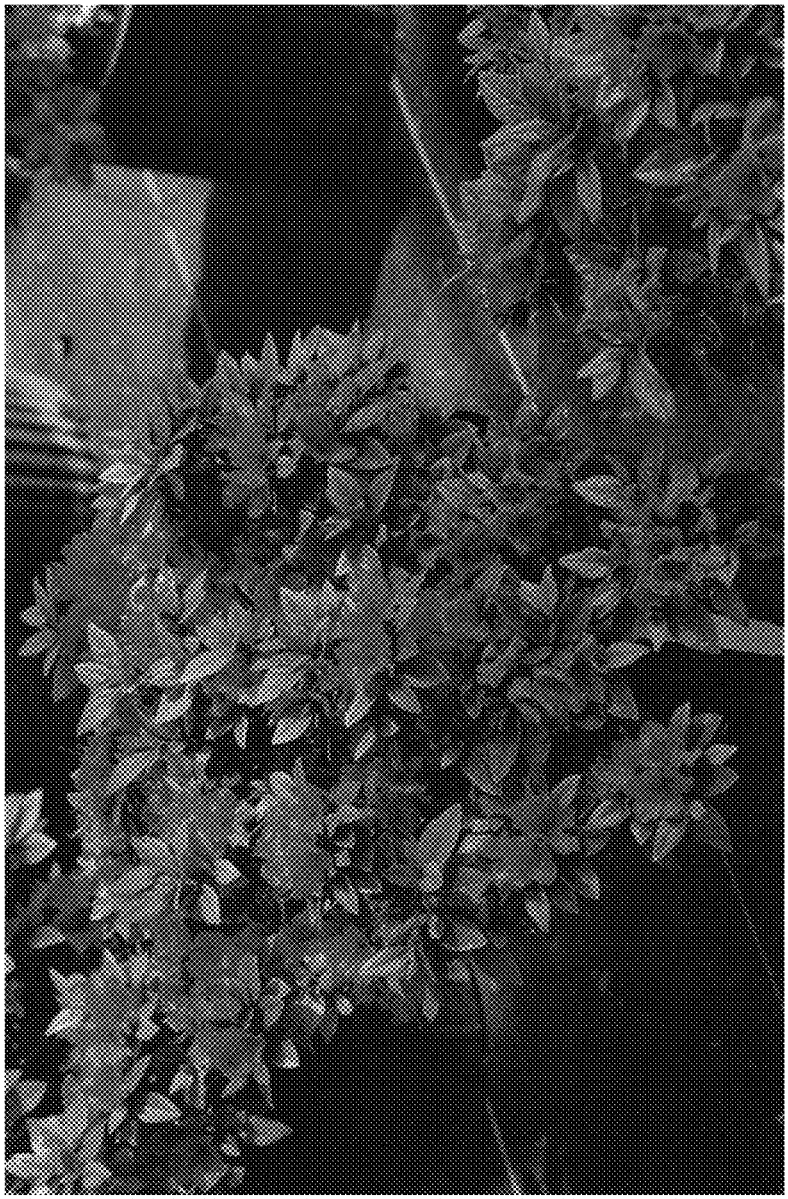
FIG. 2 Image showing a close-up of a 3-gallon plant; single bright cherry flowers visible. Image taken from 3-year-old container plants grown in Grand Haven, Mich., in 2020.

The following is a detailed description of the botanical characteristics of the new and distinct hybrid evergreen azalea known by the denomination 'NCRX8'. The detailed description was taken on a 3-year-old container-grown plant in Mills River, N.C., in 2020. Where pertinent, descriptive data was supplemented by observations/measurements taken on a 5-year-old individual located in field trials in Mills River, N.C., as well as information provided from cooperators in Grand Haven, Mich. All colors cited herein refer to The Royal Horticultural Society Colour Chart (The Royal Horticultural Society (R.H.S.), London, 2015 Edition. Where specific dimensions, sizes, colors, and other characteristics are given, it is to be understood that such characteristics are approximations or averages set forth as accurately as is practicable.

Plant:

*Plant type.*—Evergreen azalea.
*Growth habit/form.*—Globose, prostrate.
*Height at maturity.*—~75 cm.
*Width at maturity.*—~100-120 cm.
*Roots.*—Fibrous.
*Growth rate.*—Moderate.

Shoots and branches:

*Shoots* (*softwood shoots, current years growth*).—Shape: Rounded. Color: RHS Yellow-Green Group 144 C/B. Texture: Pubescent. Pubescence color: RHS Greyed-Orange Group N165B/C. Shoot diameter: 1.5-2 mm. Shoot length: Variable, ranging from ~7-15 cm.

*Shoots* (*prior-year's woody shoots*).—Shape: Rounded. Color: Mix of RHS Greyed-Orange Group 165B and RHS Grey-Brown Group N199B/C. Texture: Gently exfoliating. Stem diameter: Generally 3.5-5 mm. Stem length: Variable, ranging from 5-20 cm. Stem aspect: 0-90°.

*Branches* (*woody stems*).—Shape: Rounded. Color: Mix of RHS Greyed-Orange Group 165B and RHS Grey-Brown Group N199B/C. Texture: Exfoliating. Branch diameter: Approximately 5-10 mm. Branch length: Variable 5-15 cm. Branching: Freely branched at flowering points. Number of lateral branches: Variable, 30-70.

Foliage:

*Type.*—Evergreen.
*Arrangement.*—Alternate.
*Division.*—Simple.
*Shape.*—Elliptic to obelliptic.
*Apex.*—Mucronate.
*Base.*—Cuneate.
*Margin.*—Entire; ciliate.
*Venation.*—Reticulate.
*Internode length.*—Approximately 5-15 mm.

Immature leaf:

*Adaxial* (*upper*) *surface.*—
*Color.*—Mix of RHS Yellow-Green Group 146A/B and RHS Yellow-Green Group 147A.
*Surface.*—Pubescent.
*Abaxial* (*lower*) *surface.*—
*Color.*—RHS Yellow-Green Group 146B.
*Surface.*—Pubescent.
*Pubescence* (*same color on both sides*).—RHS Yellow-Orange Group 19C/D.

Mature leaf:

*Length.*—Approximately 3.5-6 cm.
*Width.*—Approximately 2-3.5 cm.
*Color.*—
*Adaxial* (*upper*) *surface.*—RHS Green Group 137NN A/B.
*Abaxial* (*lower*) *surface.*—RHS Green Group N138B.
*Surface.*—Both sides are lightly pubescent; RHS Greyed-Orange Group 164B/C.

Fall/winter leaf color:

*Adaxial side.*—RHS Greyed-Purple Group N186C to RHS Greyed-Purple Group 187A.
*Abaxial side.*—RHS Yellow-Green Group 149B; veins and midrib RHS Greyed- Red Group 180A.

Petiole:

*Shape.*—Lunate.
*Length.*—Approximately 5-8 mm.
*Diameter.*—Approximately 1-2 mm.
*Color.*—
*Adaxial/adaxial side.*—RHS Yellow Green Group 144A.
*Surface.*—Both sides are pubescent; RHS Greyed Orange Group 164B/C.

Flower:

*Type.*—Congested terminal raceme (truss).
*Flowering season.*—Mid-Spring (Mid-April-Early May into June) reblooms in Early Fall (Late September to through October).
*Flowering habit.*—Free-flowering.
*Flower number.*—2-5 flowers per truss.
*Consistency in display.*—Blooms reliably in the spring and consistently reblooms in the fall.
*Lastingness of flowers.*—Each flower lasts approximately 3-7 days.

*Fragrance*.—None.
*Self-cleaning or persistent*.—Self-cleaning.
Truss bud:
*Length*.—Approximately 10-18 mm.
*Diameter*.—Approximately 5-8 mm.
*Bud scales*.—
*Number*.—Variable: 4-7.
*Length*.—Approximately 8-12 mm.
*Width*.—Approximately 5-10 mm.
*Color*.—RHS Yellow-Green Group 145A/B, some bud scales deepen to RHS Red Group 46A (this is more intense in colder temperatures).
*Texture*.—Adaxial side is glabrous; abaxial side is pubescent at tip (RHS Greyed-Orange Group 164 A/B).
Emerging flowers:
*Shape*.—Elliptic, acuminate.
*Length*.—2.5-3 cm.
*Diameter*.—6-12 mm.
*Color*.—RHS Red Group 53B/C.
Perianth:
*Diameter at anthesis*.—3.5-5.5 cm.
*Depth*.—1.5-3.5 cm.
*Organization*.—Petals are arranged in a single whorl.
*Aspect*.—Facing upwards and outwards.
*Shape*.—Funnel-shaped.
*Attachment*.—Pedicellate.
Petals:
*Length*.—3-4.5 cm.
*Width*.—1.5-2 cm.
*Number*.—5.
*Shape*.—Obovate.
*Apex*.—Obtuse.
*Base*.—Acuminate
*Margin*.—Undulate.
*Fused or unfused*.—Fused at the midpoint.
*Color*.—Color is consistent from opening to anthesis. Adaxial (upper) surface: RHS Red Group 53B. Blotch: RHS Red Group 53A/B. Surface: Smooth, silky. Abaxial (lower) surface: RHS Red Group 53C/D. Dorsal Flare: Mix of RHS Red Group 42B and RHS Red Group 53 C/D. Surface: Smooth, silky.
Calyx/receptacle:
*Shape*.—Star-shaped, single-whorl of persistent sepals.
*Sepals*.—Number: 5.
*Length*.—5-10 mm. Width: 2-4 mm.
*Shape*.—Lanceolate.
*Apex*.—Cuneate.
*Margin*.—Ciliate. Color: RHS Yellow-Green Group 145A. Surface: Pubescent (RHS White Group 155C).
Pedicels:
*Shape*.—Rounded.
*Length*.—0.8-1.5 mm.
*Diameter*.—Approximately 0.5 mm.
*Color*.—RHS Red Group N45B.
*Surface*.—Both sides are pubescent (RHS White Group 155C).
Reproductive organs: Generally, flowers are both complete and perfect, although individual flowers may vary.
Gynoecium:
*Pistil number*.—1.
*Pistil length*.—3.5-5 cm.
*Stigma shape*.—Orbicular to elliptic.
*Stigma length*.—Approximately 1 mm.
*Stigma width*.—Approximately 1 mm.
*Stigma color*.—RHS Red Group 46A upon opening; RHS Red Group 53A when receptive.
*Style length*.—3-4.5 cm.
*Style diameter*.—Approximately 1 mm.
*Style color*.—RHS Red Group 46A.
*Ovary shape*.—Dome-shaped.
*Ovary length*.—3-5 mm.
*Ovary diameter*.—2.5-4 mm.
*Ovary color*.—RHS Yellow-Green Group 145A.
*Surface*.—Tomentose, RHS Yellow Group 4D.
Androecium:
*Stamen number*.—7-10.
*Anther shape*.—Ovoid with two apical pores.
*Anther attachment*.—Dorsifixed.
*Anther length*.—0.5-1 mm.
*Anther width*.—~0.5 mm.
*Anther color*.—RHS Greyed-Purple Group 183A.
*Filament length*.—2.5-4 cm.
*Filament diameter*.—Approximately 0.5-1 mm.
*Filament color*.—RHS Red Group 46B upon opening RHS Red Group 53C at anthesis.
*Amount of pollen*.—Normal.
*Pollen type*.—Vicinate.
*Pollen color*.—RHS White Group NN155.
Other characteristics:
*Fruit type*.—Capsule.
*Fruit texture*.—Pubescent/tomentose.
*Fruit length*.—Approximately 6-10 mm if successfully pollinated, ~4 mm if not.
*Fruit diameter*.—Approximately 5-10 mm if successfully pollinated, ~4 mm if not.
*Fruit color*.—
*Immature fruit color*.—RHS Yellow-Green Group 145A.
*Mature fruit color*.—RHS Brown 200D.
*Seed quantity*.—Variable 0 to hundreds.
*Seed length*.—Approximately 1 mm.
*Seed diameter*.—Approximately 0.5 mm.
*Seed color*.—
Propagation: Roots readily (>90%) from firm, terminal, softwood stem cuttings taken in mid-summer. 'NCRX8' roots well when the bottom 2 cm of the stems are treated for 5 seconds with 3,000-5,000 ppm of potassium salt of indole-3-butyric acid (KIBA) dissolved in water and placed under intermittent mist for 8-10 weeks until roots form.
Disease and insect resistance: No significant disease or insect pests have been observed.
Cold hardiness: Has been reliably cold hardy in USDA Zone 6b.

What is claimed is:

1. A new and distinct cultivar of *Rhododendron* plant named 'NCRX8' as herein illustrated and described.

* * * * *